United States Patent [19]
Connolly et al.

[11] Patent Number: 4,846,842
[45] Date of Patent: Jul. 11, 1989

[54] BODY JOINT ROTATION SUPPORT DEVICE

[75] Inventors: Donald P. Connolly, Milford; William K. McMaster, Ypsilanti, both of Mich.; William M. Hamilton, Sheffield Lake, Ohio

[73] Assignee: Connolly & McMaster, Milford, Mich.

[21] Appl. No.: 66,912

[22] Filed: Jun. 25, 1987

[51] Int. Cl.$^4$ ............................ A61F 2/64; A61F 5/04
[52] U.S. Cl. ........................................ 623/43; 623/46; 128/80 C
[58] Field of Search ................. 623/27, 39, 41, 42, 623/43, 44, 46, 59, 60; 128/80 C, 80 F; 16/374, 375

[56] References Cited

U.S. PATENT DOCUMENTS

| | | | |
|---|---|---|---|
| 37,087 | 12/1862 | Cotty | 623/46 |
| 2,812,961 | 11/1957 | Brown et al. | 623/59 X |
| 3,837,010 | 9/1974 | Prout | 623/43 X |
| 4,088,130 | 5/1978 | Applegate | 128/80 F |
| 4,337,764 | 7/1982 | Lerman | 128/80 F |
| 4,433,679 | 2/1984 | Mauldin et al. | 128/80 F |
| 4,463,751 | 8/1984 | Bledsoe | 128/80 C |
| 4,614,181 | 9/1986 | Karlsson | 128/80 C |
| 4,620,532 | 11/1986 | Houswerth | 128/80 C |

Primary Examiner—Richard J. Apley
Assistant Examiner—David J. Bender
Attorney, Agent, or Firm—Krass & Young

[57] ABSTRACT

Devices, especially orthotic, prosthetic and manipulative devices, articles of wear, and apparatus utilizing a coil spring are provided for self-adjustable support, flexion, and/or extension of limb members of a body joint. The devices have first and second support arms each having a planar face at one end joinable in co-axial face-to-face relation at a pivot point, in combination with a coplanar co-axial coil spring allowing for flexion and extension. The respective faces in one preferred embodiment have a range-of-motion guide channel and a channel-following stop member and at least one groove pair located on opposite sides of the channel for holding a stop bar across the channel to limit the range of motion of the stop member in the channel. In another preferred embodiment, one planar face has angularly spaced locking slots and the other has a pivotable locking blade that can be inserted into a selected locking slot and the edge of one of the planar faces has beveled guides enabling the coil spring under compression to be guided centrally to a position aligned with the planar faces.

14 Claims, 2 Drawing Sheets

BODY JOINT ROTATION SUPPORT DEVICE

TECHNICAL FIELD

This invention relates to devices, especially orthotic, prosthetic and manipulative devices, articles of wear, and apparatus utilizing spring means for the support, flexion, and/or extension of limb members of a body joint.

BACKGROUND ART

In the field of orthotic and prosthetic articles utilizing spring means for articulation and counter-balancing, a wide variety of devices are available. One such device which is a prosthetic joint is described in the patent to Prout, U.S. Pat. No. 3,107,358. The difficulty with conventional devices is that they are relatively complex, bulky, heavy and/or uncomfortable to wear. The devices depending on their complexity are relatively expensive and difficult to manufacture.

SUMMARY OF THE INVENTION

It is therefore an object of the present invention to provide devices, articles of wear and apparatus of the kind described which in general are less expensive and easier to manufacture than conventional devices.

It is a further object of the invention to provide devices, articles of wear, and apparatus of the kind described having simple components that are interchangeable and provide for lateral or medial support, right and left handed support, and variation in flexion and extension force.

These and other objects, features and advantages will be seen from the following description and accompanying drawings in which:

DETAILED DESCRIPTION OF THE PREFERRED EMBODIMENT

Figure 1:
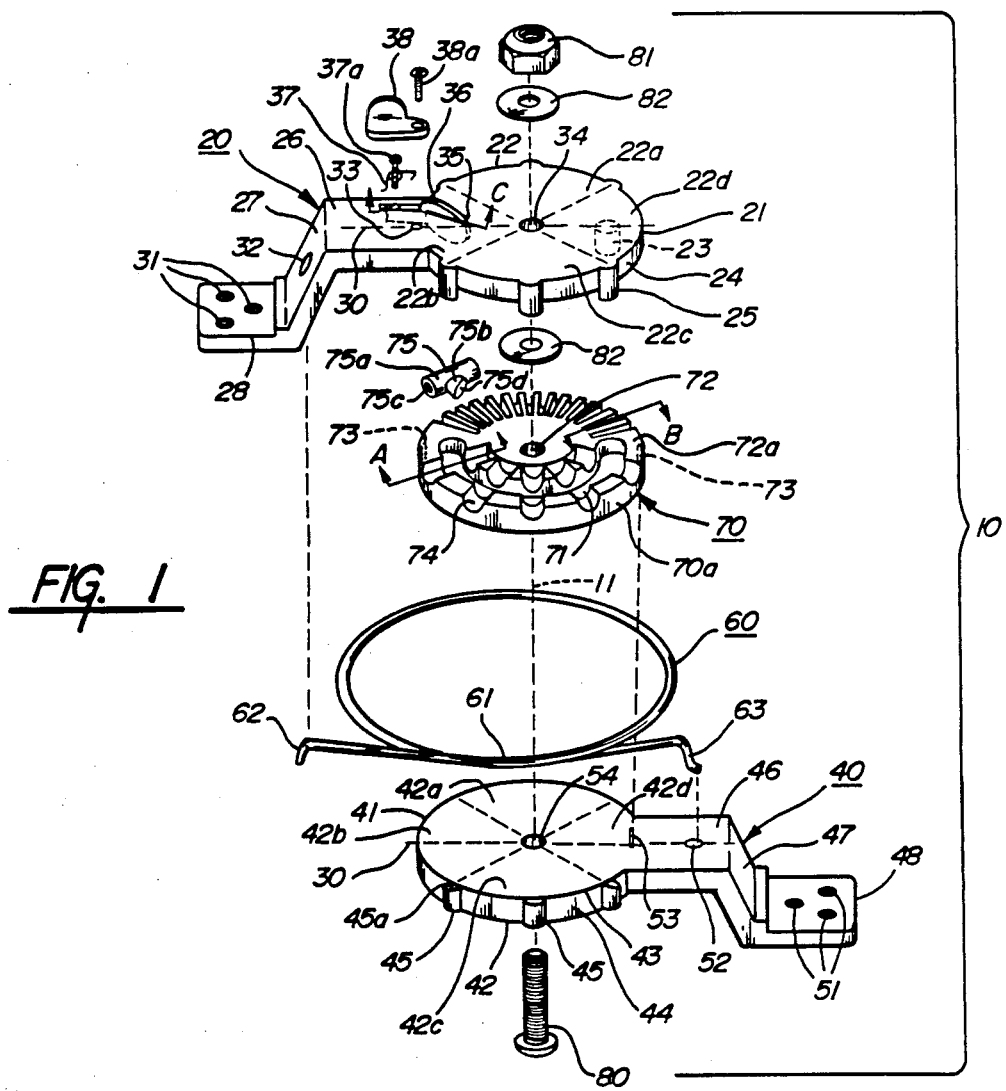
FIG. 1 is an exploded view in perspective of a preferred embodiment of a support device according to the invention.

In a preferred embodiment, the invention comprises a support device for controlled flexion and/or extension of limb members of a body joint, including first and second support arms, a pivotal connection for the support arms, and a coil spring, preferably an open coil spring, biasing the support arms under extension. The first and second support arms can be thought of as lower and upper support arms where, viewed for example as a lateral support for the right knee joint, the overlap of the coil spring (FIG. 1) occurs at the knee-cap side of the joint, i.e., the side away from that toward which the joint is flexed. The support arms each have a proximal end and a distal end, each of which arms can include conventional elements for securing the same to the body. The proximal ends each have a circular hub, each of which in turn has a planar face such that the proximal ends are joinable in coaxial face-to-face relation at a pivot point allowing for limb-supporting flexion and/or extension of the support arms. The respective faces of the support arms include a circumferential range-of-motion guide channel and a channel-following stop member that is received and moveable in said channel under flexion and extension such that the magnitude of flexion and/or extension is controlled by the effective length of the guide channel. The coil spring (which may be one or more coils) is in alignment that is a substantially co-planar and co-axial alignment with the planar faces. The mentioned components are dimensioned such that when the coil spring biases the support arms under extension, the coil is larger than the circumference of the hub and when the support arms are placed under a continued flexioning force the coil can be made progressively smaller until its inside diameter approximates the circumference of the hub.

The hub and its planar face including the guide channel can be unitary. In a preferred embodiment, the hub and the planar face are separate elements having means for co-axially locating the hub and planar face at different fixed points of angularly rotation (e.g. as a face-plate held on a pin — as in FIG. 1) with respect to each other. In a preferred form, the planar face or face-plate can be so held by means of a pin-hole or blind hole at either end of a diameter whereby the hub and its planar face are reversible such that the device can be employed interchangeably for either the medial support or the lateral support of a limb member. A similar embodiment uses an off-center locator pin as part of the hub element and further comprises diametrically opposed locator pin channels as part of the planar face element such that the elements can be assembled interchangeably in either zero degree rotation or 180 degree rotation. In a preferred embodiment, the guide channel in the planar face is of a length such that the channel and stop member accomodate rotation through an angle up to about 180°.

In a preferred support device, the planar face including the guide channel comprises at least one radially oriented groove pair located on opposite sides of the channel for holding therebetween a stop bar across the channel such that the stop member of the other planar face is blocked from further movement in the channel thereby controlling the effective length of the guide channel. Preferably, the guide channel comprises a plurality of groove pairs that are radially spaced apart from each other whereby a stop bar can be inserted and held in a selected one of said groove pairs to thereby control stop member movement to that particular desired length of the guide channel. In a preferred embodiment, the stop bar is a T-bar of which the T-cross bar is located in a position bridging the channel and the base or stub bar portion of the T-bar is disposed in the channel in a direction forward of or trailing the front edge of the cross bar to corresponding shorten or lengthen the guide channel. In a preferred embodiment, the outside end of the T-cross bar includes access means such as an Allen wrench slot for rotating the cross bar so that the base of the T-bar can be disposed to either a forward or a trailing position whereby rotation thereof serves to change the effective length of the guide channel. The invention contemplates that the device apparatus can be assembled respectively as a lateral and medial pair of devices for the lateral and medial support of limb members of a body joint.

A preferred support device according to the invention is one where the one planar face including a guide channel also has a separate face portion including a plurality of angularly spaced radially oriented locking slots and the hub that includes the other planar face has in combination a pivot-mounted locking blade and a radially oriented blade slot adapted to receive the locking blade such that when the blade slot and one of the locking slots are in radial alignment, the locking blade can be inserted into said aligned locking slot whereby the support arms of the device can be locked in the corresponding fixed position of flexion or extension.

Another preferred embodiment of a support device includes first and second support arms each having a proximal end and a distal end, the proximal ends each comprising a circular hub having a planar face such that the proximal ends are joinable in coaxial face-to-face relation at a pivot point allowing for limb-supporting flexion and/or extension of said support arms, one of said planar faces including a plurality of angularly spaced radially oriented locking slots corresponding to positions of flexion or extension and the hub that includes the other planar face having in combination a pivot-mounted locking blade and a radially oriented blade slot adapted to receive the locking blade such that when the blade slot and one of the locking slots are in radial alignment, the locking blade can be inserted into said aligned locking slot whereby the support arms of the device can be locked in the corresponding fixed position of flexion or extension. The preferred embodiment may include as an option spring means such as coil spring means biasing said support arms under extension, said spring means being substantially in coplanar and co-axial alignment with said planar faces and dimensioned such that when biasing the support arms under extension the coil is larger than the circumference of the hub and when the support arms are placed under a continued flexioning force the coil can be made progressively smaller until its inside diameter approximates the circumference of the hub.

The hub and its planar face including the locking slots can be unitary, and in a preferred form they are separate elements having means for locating said hub and planar face at different fixed points of angularly rotation (e.g. as a face-plate held on a pin as in FIG. 1), with respect to each other. In a preferred form, the planar face or face-plate can be so held by means of a pin-hole or blind hole at either end of a diameter whereby the hub and its planar face are reversible such that the device can be employed interchangeably for either the medial support or the lateral support of a limb member or as a lateral and medial pair of devices for both lateral and medial support of a body joint. Preferably, the locking slots are evenly spaced and of a range such that fixed position locking is provided at any one flexioning angle from zero to about 150 degrees.

Referring now to the drawings, a preferred embodiment of a support device 10 according to the invention, is shown in FIG. 1. The device includes a first or outer support arm 20, a second or inner support arm 40, a coil spring 60, a face plate 70, and securing means including a bolt 80, nut 81, and washers 82. The support arms 20, 40 each have a proximal end 21, 41 including a hub 22, 42 and shank portion 26, 46. The hubs 22, 42 and the face plate 70 comprise 4 quadrants, for convenience designated in dotted outline for these hubs 22, 42 in what may be described respectively as rear quadrants 22a, 42a, lower quadrants 22b, 42b, front quadrants 22c, 42c, and upper quadrants 22d, 42d. The hub edges 24, 44 are provided with guide figures or projections 25, 45 that are evenly spaced apart along the opposing front and rear quadrants for purposes presently to be described.

Referring further to FIG. 1, the support arms have upper offsets 27, 47 and lower offset distal ends 28, 48. The outer support arm 20 on or near its mid-line 30 is provided with attachment through-holes 31, a spring anchor hole 32, a latch anchor hole 33, and a central pivot hole 34. The support arm 20 also is provided with a stop or stud member 23 (shown in dotted outline), a blade slot 35, a locking blade 36, a blade-bias spring 37, a blade pivot screw 37a, a wiper blade 38 and a wiper pivot screw 38a.

Figure 1A:
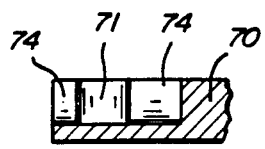
FIGS. 1A, 1B and 1C are sectional views of the device taken on lines A—A, B—B and C—C OF FIG. 1.
Figure 1B:
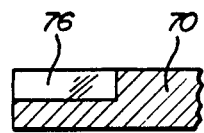
Figure 1C:
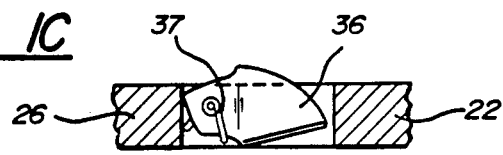
Figure 2:
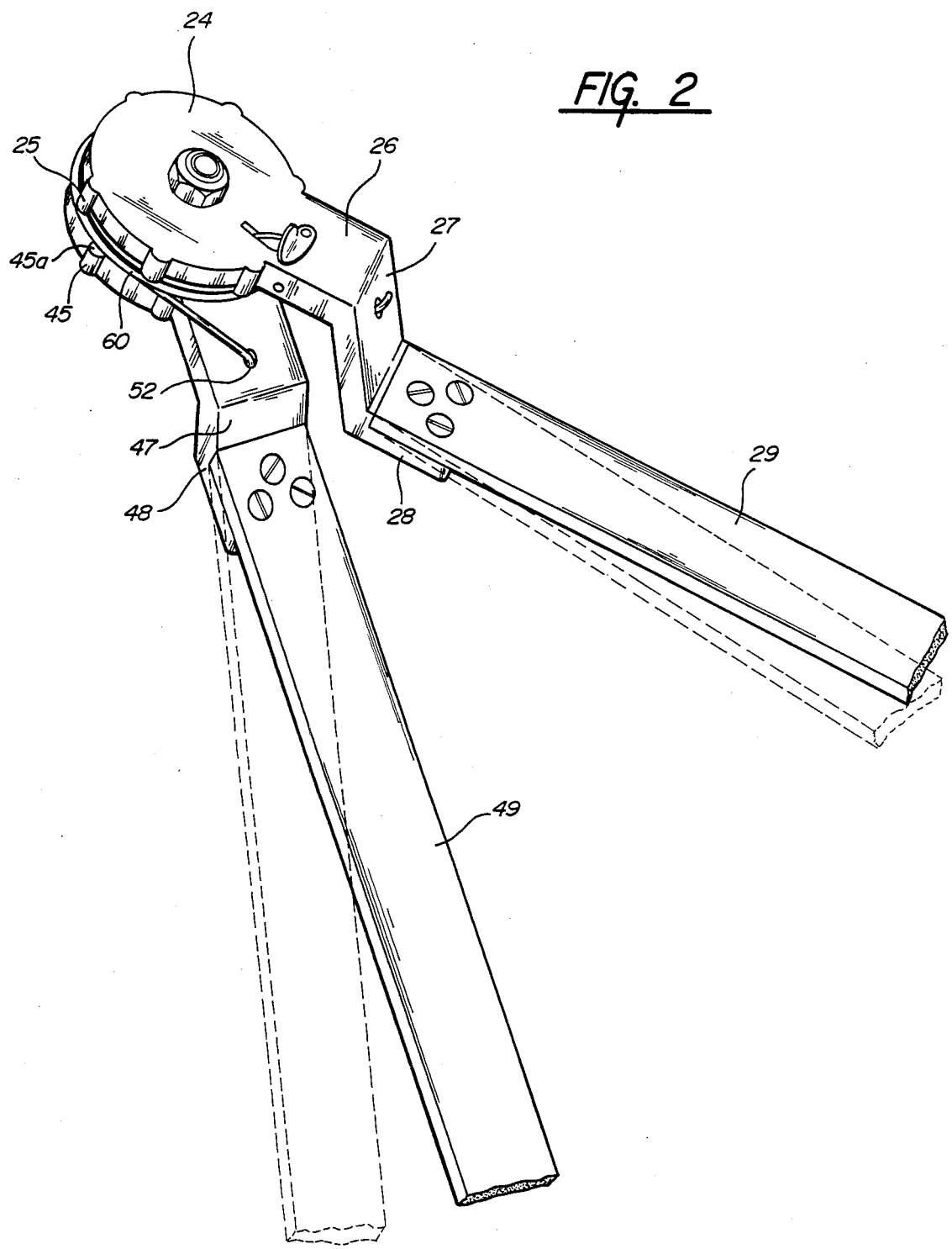
FIG. 2 is a view in perspective of a device in a position of full flexion.

The inner support arm 40 on or near its mid-line 30 is provided with attachment through-holes 51, a spring anchor hole 52, a plate attachment pin 53, and a central pivot hole 54. For interchangeable attachment to the face 43 of the support arm is the mentioned face plate or disk 70. The face plate is provided with a circumferential channel 71 extending through two quadrants for about 180 degrees, a central pivot or anchor hole 72, and pin recess holes 73 located at opposite ends of the mid-line and shown in dotted outline. The channel curvature is such that it accomodates free movement of the stop member 23 when the hub 22 and the face plate 70 undergo rotation relative to each other. The face plate is also provided with spaced pairs of saddle grooves 74, 74 (FIG. 1A) and a T-bar 75 configured with its cross bar 75a to lie across the channel 71 in matching fit in the saddle groove pair. The base 75b of the T-bar can be oriented forwardly in the channel as shown or the cross bar 75a can be rotated 180 degrees by means of a tool (e.g. an Allen wrench) inserted in a tool-receiving end recess 75c so that the base 75b of the T-bar is moved to a trailing position. In the former case the detent surface is the lower surface 75d of the T-bar and in the latter case the cross bar 75a itself. Thus, the T-bar can serve interchangeably as a detent or stop in either of two positions. Since the face plate 70 as shown has five spaced saddle groove pairs, it can be these means provide a total of ten different stop positions with corresponding angular spacing along the length of the channel. As a preferred feature, the support device is provided with means for locking the support arms in a fixed position so that rotation is prevented. For this purpose, the face plate 70 includes a fan-shape series of angularly spaced locking slots 76 (seen in cross-section, FIG. 1A) each of which functions with the previously mentioned locking blade 36 and wiper blade 38 to engage and hold the blade so that in turn the support arms are locked in one position which as desired can be a position of full extension or of partial or full flexion (as in FIG. 2). For this purpose, the position for lock-up is selected by the wearer, and the wearer then manually advances the wiper blade 38 from the open position shown so that it pivots onto the locking pivot blade 36 and depresses the blade into the appropriate slot 76 therebelow. Release of the wiper blade from the locking position to the open position shown allows the locking blade to pivot back to the stop position or unlocked position (shown in FIG. 1C) since it is under constant upward bias of the control spring 37. As shown, the blade in the unlocked position is prevented from further upward movement by its contact with the adjacent wall of the blade slot 35.

In use, the support device can be employed as part of an orthotic or prosthetic appliance by suitable attachment serving in support of a body joint or in place of a body joint. The device can, for example, use extension bars 29, 49 as in FIG. 2, held in place medially or laterally on the body member by suitable means such as adjustable strapping, belts and the like. The extension bars 29, 49 can be secured (by threadably engaged screw means or other suitable means) in alignment and in the same plane with the lower offset distal ends 28, 48 (as shown in solid outline) or in a preferred embodiment can be out of alignment (in the same plane, as shown in dotted outline) and thus by choice can be reversed to the left or right alignment as desired. The device can be used for any of various body joints including the elbow, knee, ankle, finger, foot or hip. The device can be made of any of various art recognized materials.

In this regard, the main parts of the device can be of cast metal (e.g., bronze or brass) construction, particularly the two opposing offset arms, and the adjustable disk which converts the arms to either right or left handed function. Exposed parts such as the arms are preferably curved to avoid sharp edges.

These three parts in a preferred embodiment all have a centrally located pivot hole (each one-quarter inch in diameter) held together with a pin head machine threaded bolt with an aircraft-type nylon insert nut. The two arms and adjustable disk have two low-friction plastic washers, one between the adjustable disk and the upper larger offset arm and the other between the upper offset arm and the aircraft-type nut. The coil spring in a preferred form is a one-coil spring of round piano wire with differently shaped ends as shown which will allow the spring to be held centrally around the hub pivot area when inserted in holes located in each opposing arm. The flexibility of the coil spring is selected to achieve the desired extension work force that keeps the coil open when not compressed. It is found that piano wire having about 46 mil thickness made up in a one-coil spring as shown and being about one-and-seven-eighths inch in loop diameter requires a force of about 7½ pounds to achieve full compression to the position shown in FIG. 2 (for a device used without the extension bars 29, 49). In order to maintain the coiled spring parallel to the narrow edge of the arms, there are half round projections at right angle to the edges of the upper and lower arms and spaced nearly equidistant from one another and each has an end bevel 45a favoring the central disk edge that will guide the coiled spring over the flat of the central disk edge while the device is rotated to bring the spring under partial or full compression. Further, these right angled edge projections are of different lengths. The projections of the lower arm are of the same thickness as the cross section, but as indicated have a bevel on the end favoring the central disk. The projections of the upper arm are longer so that they will be down further than the top surface of the central disk so the spring cannot be jammed between the upper arm and center disk surfaces during rotation. The diameter of the center disk is also smaller than the upper and lower circular diameters so the inner edge of the upper arm vertical projections will allow the central disk outside edge to freely rotate within the overhanging projections.

Having thus described our invention, the embodiments are not limited to a single form and include other embodiments within the scope of the claims as follows.

We claim:

1. A support device for controlled flexion and/or extension of limb members of a body joint, including;

first and second support arms each having a proximal end and a distal end, the proximal ends each comprising a circular hub having a planar face such that the proximal ends are joinable in co-axial face-to-face relation at a pivot point allowing for limb-supporting flexion and/or extension of said support arms, the respective faces of said first and second support arms including a circumferential range-of-motion guide channel and a channel-following stop member that is received and movable in said channel under flexion and extension such that the magnitude of flexion and/or extension is controlled by the effective length of the guide channel, the guide channel comprising at least one radially oriented groove pair located on opposite sides of the channel for holding therebetween a stop bar across the channel such that said channel-following stop member is blocked from further movement in said channel, a pivotal connection for said support arms, and coil spring means biasing said support arms under extension, said spring means being substantially in co-planar and co-axial alignment with said planar faces and dimensioned such that when biasing the support arms under extension the coil is larger than the circumference of said hubs and planar faces and when the support arms are places under a continued flexioning force the coil can be made progressively smaller until its inside diameter more closely approximates the circumference of said hubs and planar faces.

2. A support device according to claim 1 where the hub of one of said arms and its planar face including the guide channel are separate elements having means for co-axially locating said hub and planar face at different fixed points of angular rotation with respect to each other.

3. A support device according to claim 2 where said hub and its planar face are reversible such that the device can be employed interchangeably for either the medial support or the lateral support of a limb member.

4. A support device according to claim 2 where said locating means comprises an off-center locator pin as part of the hub element and further comprises diametrically opposed locator pin channels as part of the planar face element such that said elements can be assembled interchangeably in either zero degree rotation of 180 degree rotation.

5. A support device according to claim 1 where the guide channel and stop member accomodate rotation through an angle up to about 180°.

6. A support device according to claim 1 where the spring means is dimensioned such that the coil can be made progressively smaller until at full flexion its inside diameter approximates the circumference of said hubs and planar faces.

7. A support device according to claim 1 where the guide channel comprises a plurality of groove pairs that are angularly spaced apart from each other whereby a stop bar can be inserted and held in a selected one of said groove pairs to control the desired length of the guide channel.

8. A support device according to claim 1 including a stop bar where said stop bar is a T-bar of which the T-cross bar is located in a position bridging the channel and the base of the T-bar is disposed in the channel in a direction forward of the front edge of the cross bar.

9. A support device according to claim 8 where the outside end of the T-cross bar includes access means for rotating the cross bar so that the base of the T-bar can be disposed to a forward or a trailing position whereby rotation thereof serves to change the effective length of the guide channel.

10. A support device according to claim 1 including a stop bar where said stop bar is a T-bar of which the T-cross bar is located in a position bridging the channel and the base of the T-bar is disposed in the channel in a direction trailing the front edge of the cross bar.

11. A support device according to claim 1 including angularly spaced slots for locking said support arms in a fixed position of flexion or extension.

12. A support device according to claim 1 where the one planar face including the guide channel also has a separate face portion including angularly spaced locking slots each corresponding to a position of flexion or extension and the hub that includes the other planar face has in combination a pivot-mounted locking blade and an angularly oriented blade slot adapted to receive the locking blade such that when the blade slot and one of the locking slots are in alignment the locking blade can be pivotably inserted into said aligned locking slot whereby the support arms of the device can be locked in said corresponding position of flexion or extension.

13. A support device for controlled flexion and/or extension of limb members of a body joint, including;

first and second support arms each having a proximal end and a distal end, the proximal ends each comprising a circular hub having a planar face such that the proximal ends are joinable in co-axial face-to-face relation at a pivot point allowing for limb-supporting flexion and/or extension of said support arms, the respective faces of the support arms including a circumferential range-of-motion guide channel and a channel-following stop member that is received and movable in said channel under flexion and extension such that the magnitude of flexion and/or extension is controlled by the effective length of the guide channel, the guide channel comprising at least one radially oriented groove pair located on opposite sides of the channel for holding therebetween a stop bar across the channel such that the stop member of the other planar face is blocked from further movement in said channel, a pivotal connection for said support arms, and coil spring means biasing said support arms under extension, said spring means being substantially in coaxial alignment with said planar faces.

14. A support device for controlled flexion and/or extension of limb members of a body joint, including;

first and second support arms each having a proximal end and a distal end, the proximal ends each comprising a circular hub having a planar face such that the proximal ends are joinable in co-axial face-to-face relation at a pivot point allowing for limb-supporting flexion and/or extension of said support arms, coil spring means biasing said support arms under extension force in co-axial alignment with said planar faces, one of said planar faces including angularly spaced locking slots corresponding to positions of flexion or extension and the hub that includes the other planar face having in combination a pivot-mounted locking blade, a retractable wiper blade for wiping the locking blade from an open position into a locking position, means biasing the locking blade into said open position, and a blade slot adapted to receive the locking blade such that when the blade slot and one of the locking slots are in alignment the locking blade can be inserted into said aligned locking slot by means of the wiper blade whereby the support arms of the device by means of the coil spring biasing said arms and planar faces under extension can be maintained locked in a corresponding position of flexion or extension, and further such that when the wiper blade is retracted the locking blade is biased into said open position, and a pivotal connection for said support arms.

* * * * *

UNITED STATES PATENT AND TRADEMARK OFFICE
CERTIFICATE OF CORRECTION

PATENT NO. : 4,846,842

DATED : July 11, 1989

INVENTOR(S) : Connolly et al.

It is certified that error appears in the above-identified patent and that said Letters Patent is hereby corrected as shown below:

Column 6, line 43, "of" should be --or--.

Signed and Sealed this

Eighth Day of October, 1991

Attest:

HARRY F. MANBECK, JR.

*Attesting Officer*  *Commissioner of Patents and Trademarks*